(12) United States Patent
Yatsui et al.

(10) Patent No.: US 7,821,267 B2
(45) Date of Patent: Oct. 26, 2010

(54) MAGNETIC RESONANCE IMAGING METHOD AND APPARATUS

(75) Inventors: Yumiko Yatsui, Toyokawa (JP); Koji Kajiyama, Kamagaya (JP); Hideki Kumai, Kashiwa (JP); Tetsuhiko Takahashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 426 days.

(21) Appl. No.: 11/916,130

(22) PCT Filed: May 30, 2006

(86) PCT No.: PCT/JP2006/310716
§ 371 (c)(1),
(2), (4) Date: Nov. 30, 2007

(87) PCT Pub. No.: WO2006/132104
PCT Pub. Date: Dec. 14, 2006

(65) Prior Publication Data
US 2009/0309595 A1    Dec. 17, 2009

(30) Foreign Application Priority Data
Jun. 9, 2005    (JP) .............................. 2005-169812

(51) Int. Cl.
*G01V 3/00* (2006.01)
(52) U.S. Cl. .................. 324/318; 324/322; 600/410
(58) Field of Classification Search ............... 324/318, 324/322; 600/410
See application file for complete search history.

(56) References Cited

U.S. PATENT DOCUMENTS

| 6,479,996 | B1 | 11/2002 | Hoogeveen et al. |
| 7,474,912 | B2 * | 1/2009 | Lehtonen-Krause ........ 600/410 |
| 7,486,076 | B2 * | 2/2009 | Nagao et al. ................. 324/318 |
| 7,635,979 | B2 * | 12/2009 | Takizawa et al. ............ 324/309 |
| 7,659,720 | B2 * | 2/2010 | Furudate et al. ............. 324/318 |
| 2002/0087069 | A1 | 7/2002 | Ho et al. |
| 2002/0115929 | A1 | 8/2002 | Machida |
| 2004/0081341 | A1 | 4/2004 | Cherek et al. |

FOREIGN PATENT DOCUMENTS

| JP | 2002-95646 | 4/2002 |
| JP | 2002-315735 | 10/2002 |
| JP | 2004-49911 | 2/2004 |
| JP | 2004-503270 | 2/2004 |
| JP | 2004-236849 | 8/2004 |

* cited by examiner

*Primary Examiner*—Louis M Arana
(74) *Attorney, Agent, or Firm*—Cooper & Dunham LLP

(57) ABSTRACT

In an imaging according to the step moving method, a slice imaging condition with respect to each station is optimized, thereby enabling an efficient imaging. A controller of an MRI apparatus displays positioning frames 601 to 606, and operation handles 607 and 608 thereof, in order to set a slice imaging condition at every various positions (stations) of a table on which a test object is mounted. By manipulating the positioning frames and the operation handles via I/O unit, the slice imaging condition is set. According to this slice imaging condition, imaging at each station position of the table is executed.

22 Claims, 13 Drawing Sheets

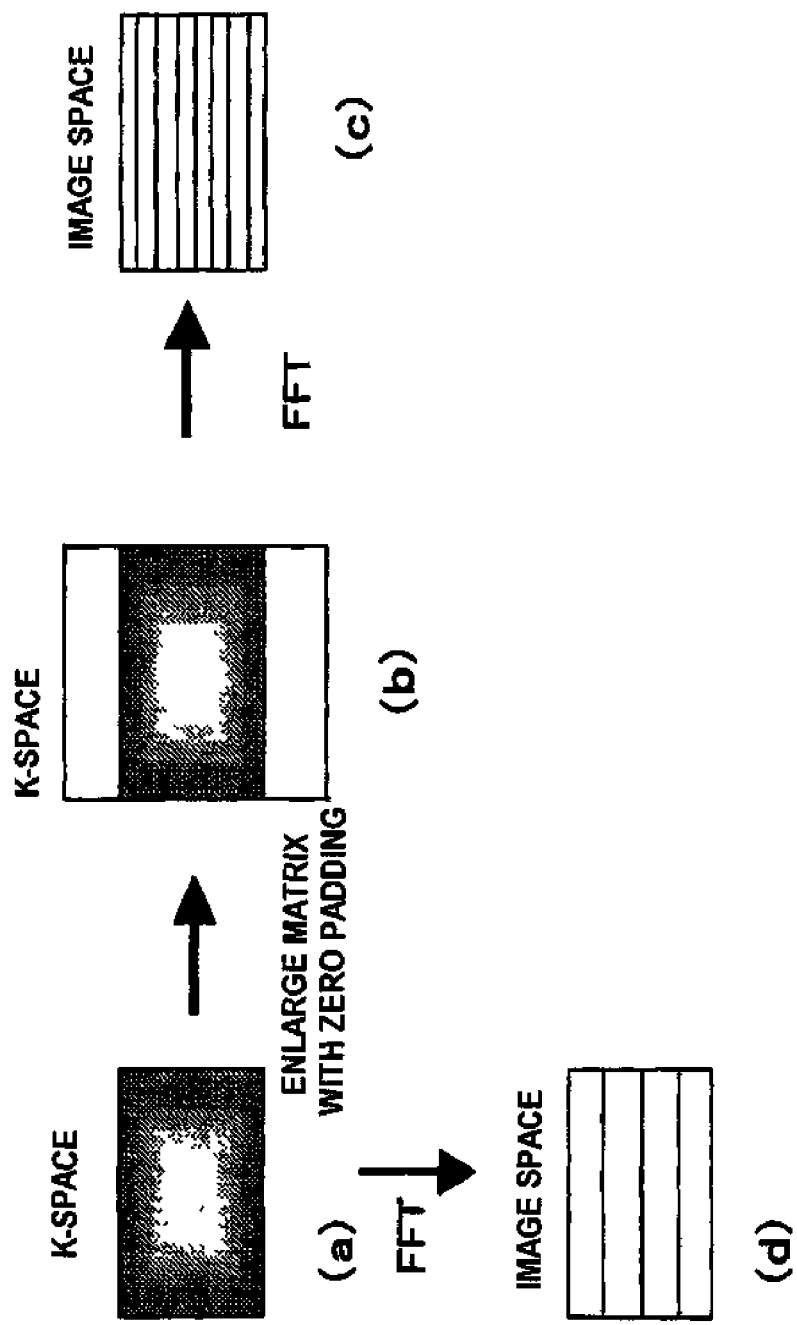

MAGNETIC RESONANCE IMAGING METHOD AND APPARATUS

TECHNICAL FIELD

This disclosure relates to a magnetic resonance imaging apparatus (hereinafter, referred to as "MRI apparatus"). More particularly, it relates to an MRI apparatus in which a table mounting a test object thereon is moved among multiple stations, and images respectively taken on the stations are synthesized to obtain a wide field image of the test object.

BACKGROUND ART

The MRI apparatus is an apparatus to take an image of the test object by obtaining a signal using a nuclear magnetic resonance from the test object placed in a static magnetic field space. The imaging space is limited to an area where the static magnetic field generated by a static magnetic field magnet is highly homogeneous. In order to obtain an image having a range equal to or larger than the maximum field that can be taken as an image by the MRI as described above, following method is induced: initially, a part of the image of the test object is acquired; subsequently the table on which the test object is mounted is moved to take another part of the image; this procedure is repeated and the obtained parts are pieced together (e.g., Patent document 1). This method is referred to as a multi-station imaging or a step shift method (in this example here, it is referred to as "step shift method").

The patent document 1 describes a method for imaging of vasculature according to the step shift method, and in particular, considering movement of a contrast agent in the body axial direction of the test object, a spatial resolution of the imaging is varied station by station.

[Patent Document 1]

Japanese Published Unexamined Patent Application No. 2002-315735

In imaging according to the step shift method, in many cases, imaging of each station is performed by a multi-slice imaging or a 3D imaging. In such a case, the imaging is carried out under an identical condition where a number of slices and/or a number of slice encodings are preset. However, if a test object which varies in size along the moving direction of the table is a target of the imaging, the imaging is performed even in an area where the test object does not exist, in many cases. Therefore, imaging efficiency is not good. When a part of the test object is curved with respect to the slice surface, it is necessary to take an image of a large number of slices including many regions where the test object does not exist. The present applicant suggests a technique in which basic information such as the size and inclination of the test object is inputted, and the imaging is performed based on this information (patent document 2). This technique enables an optimum imaging that fits the size and inclination of the test object. However, it is further demanded to facilitate the slice setting, considering the settings in each station and a linkage between the stations in the multi-slice imaging.

[Patent Document 2]

International Publication WO 2006/041084

SUMMARY

In an aspect of this disclosure, an MRI method and apparatus are provided for optimizing a station-by-station slice imaging condition and also simplifying the setting of the station-by-station slice imaging condition, in an imaging according to the step shift method.

In another aspect there is provided an MRI method that moves a test object in a stepwise manner among multiple stations, and takes images of different areas of the test object on the respective stations, so as to acquire an image of a wide range of the test object, including, a slice imaging setting step for performing a slice imaging setting by arranging a positioning frame of a slice for each of the stations, using a positioning image that is previously acquired and includes the wide range, an imaging step for performing imaging in each of the stations based on the slice image setting of each of the stations, and a synthesizing step for synthesizing a test object image of the wide range by using a nuclear magnetic signal obtained by the imaging step, wherein, in the slice imaging setting step, the positioning frame being arranged is adjusted according to how to place the test object.

The adjustment of the positioning frame includes, for example, movement of the positioning frame in a slice direction or in a direction orthogonal thereto, deletion or addition of the slice, and a change of a slice thickness within the positioning frame, a change of field-of-view (FOV) of the positioning frame, and the like. The adjustment of the positioning frame is configured in such a manner that it is independent with respect to each station, or there is a linkage among the stations.

In another aspect there is provided an MRI apparatus that includes, a static magnetic field generation means for generating a static magnetic field, a transfer means for moving a test object in the static magnetic field space generated by the static magnetic field generation means, an imaging means for moving the test object in a stepwise manner among multiple stations and taking an image using a nuclear magnetic resonance, an image reconstruction means for creating an image of a wide range of the test object based on the nuclear magnetic resonance signal acquired in each of the multiple stations, a control means for controlling the transfer means, the imaging means, and the image reconstruction means, a slice imaging setting means for performing a slice image setting by arranging a slice positioning frame for each of the stations, using a positioning image previously acquired and including the wide range, and an input means for inputting a directive to the slice imaging setting means, wherein, the control means exercises control so that the imaging means takes an image of the slice that is set by the slice imaging setting means. On this occasion, the slice imaging setting means adjusts the positioning frame being arranged, based on the directive inputted from the input means. In the MRI apparatus according to the present invention, the positioning frame is configured in a manner as being subject to change, such as parallel shift, rotation, and scaling. The MRI apparatus according to the present invention is further provided with a means for adjusting each of the positioning frame independently (a first handle), and a means for adjusting the positioning frame in linked manner one with another (a second handle).

By adjusting the positioning frame, it is possible to adjust the number and the position of the slices to be subjected to imaging at every position of the transfer means, a wasteful imaging such as imaging a region where the test object does not exist can be eliminated, and therefore an efficient total body imaging can be carried out. In addition, by adjusting the inclination of the slice, most appropriate imaging slice can be configured, in such a manner that it fits the test object's posture and curved shape, and therefore further efficient total body imaging can be achieved.

BRIEF DESCRIPTION OF DRAWINGS

FIG. 13 illustrates the interpolation in the 3D imaging.

100 . . . IMAGING SYSTEM, 200 . . . CONTROLLER, 210 . . . IMAGING CONTROLLER, 220 . . . IMAGE RECONSTRUCTION UNIT, 230 . . . TABLE CONTROLLER, 240 . . . DISPLAY CONTROLLER, 250 . . . STORAGE UNIT, 300 . . . I/O UNIT

DETAILED DESCRIPTION OF PREFERRED EMBODIMENT

Figure 1:
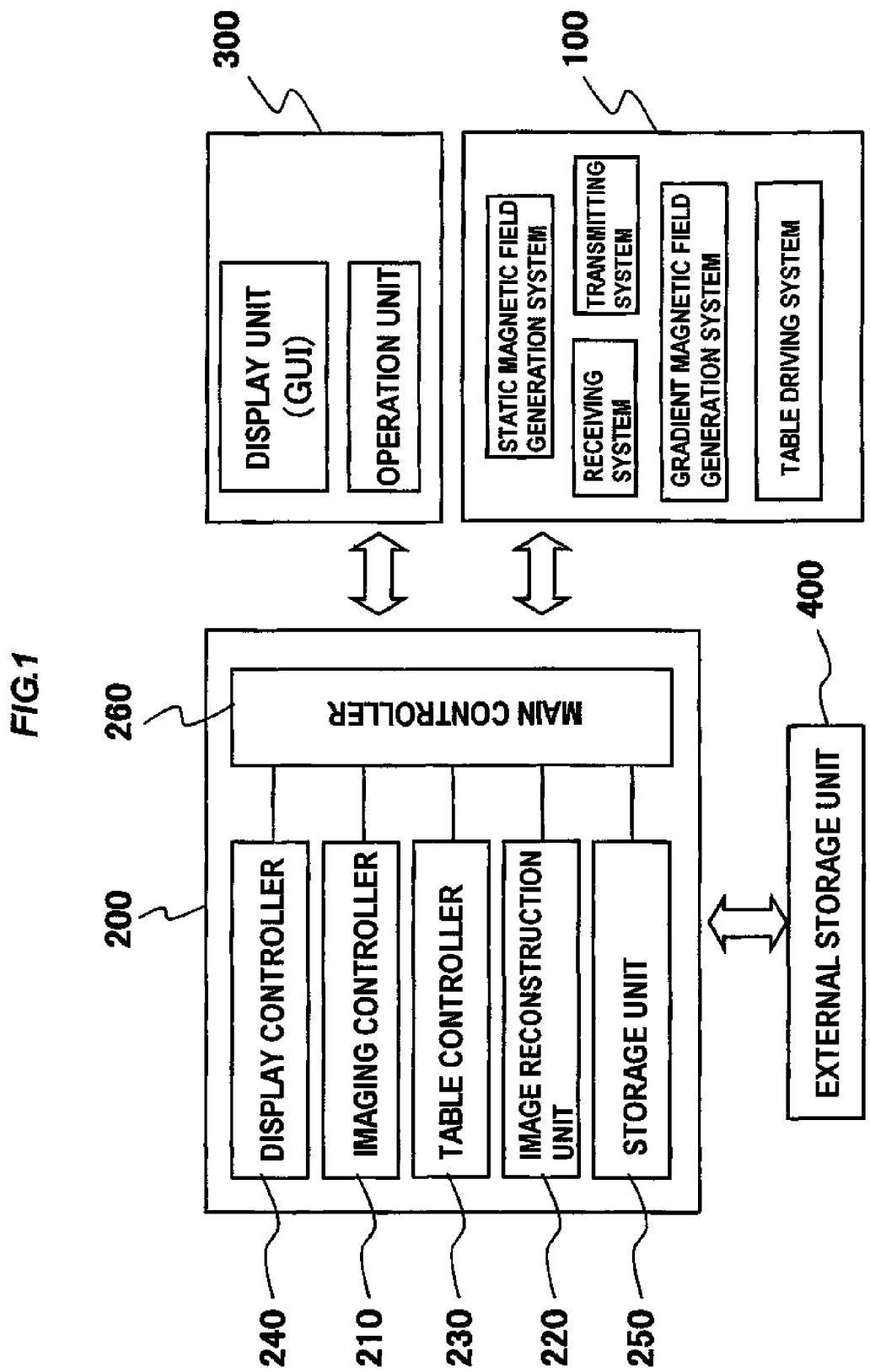
FIG. 1 is a block diagram showing a total configuration of an MRI apparatus according to the present invention.
Figure 2:
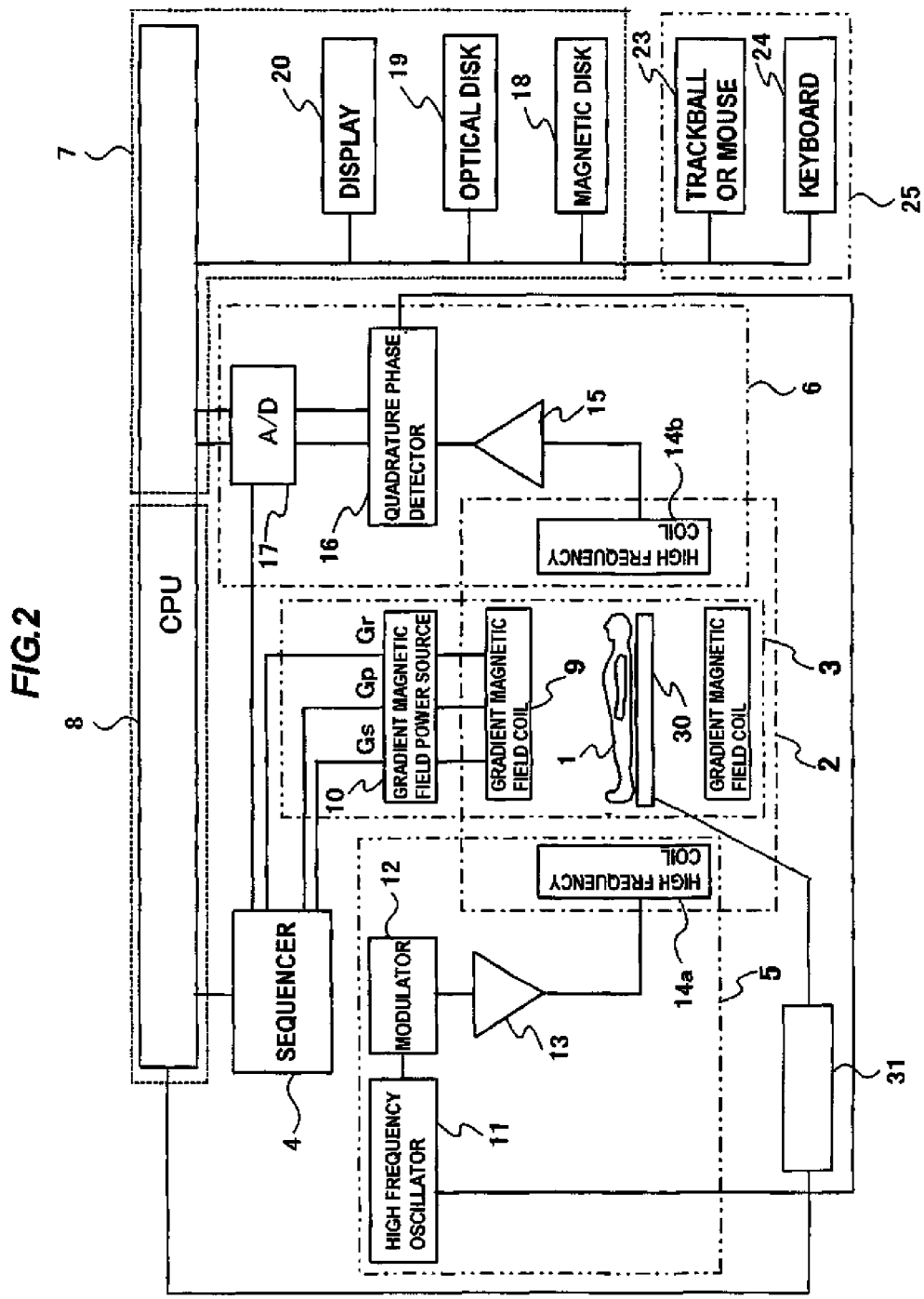
FIG. 2 illustrates constitutional elements of the MRI apparatus according to the present invention.

Hereinafter, a preferred embodiment will be explained with reference to the accompanying drawings. FIG. 1 is a block diagram showing an overview of an embodiment of the MRI apparatus according to the present invention. FIG. 2 is a block diagram showing a main configuration thereof. This MRI apparatus includes an imaging unit 100 for taking an image of the test object as a main function, a controller 200 for controlling device and performing a signal processing such as image reconstruction, an I/O unit 300 including an operation part for accepting a directive from an operator, and a display unit (display) for displaying an image, a GUI, or the like, which are obtained by the imaging, and an external storage unit 400 such as a magnetic disk and an optical disk.

As shown in FIG. 2, the imaging unit 100 is provided with a static magnetic field generation system 2 for generating a homogeneous static magnetic field within a space (imaging space) where the test object 1 is placed, a gradient magnetic field generation system 3 for generating a gradient magnetic field in the imaging space, a transmitting system 5 for applying a high frequency magnetic field for exciting a nucleus of an atomic element constituting a tissue of the test object 1, a receiving system 6 for receiving a nuclear magnetic resonance signal (NMR signal) generated from the test object 1, and a table driving system 31 for moving the table 30 on which the test object 1 is laid.

The static magnetic field generation system 2 generates a homogeneous magnetostatic field in a body axis direction or in a direction orthogonal to the body axis in the space surrounding the test object 1, employing a magnetic field generation means such as a permanent magnet system, a normal conducting system, or a superconducting system.

The gradient magnetic field generation system 3 is made up of the gradient magnetic field coils 9 wound in the three axial directions X, Y, and Z, and gradient magnetic field power source 10 that drives each of the gradient magnetic field coils, and gradient magnetic fields Gs, Gp, and Gr are generated in desired directions within the static magnetic field space by driving the gradient magnetic field power source 10 for each of the gradient magnetic field coils, in response to a command from the sequencer 4. According to the way applying these gradient magnetic fields, an imaging section (slice plane) of the test object 1 is selected, and positional information (phase-encoding, frequency-encoding, and the like) can be added to the nuclear magnetic resonance signal (echo signal) generated from the test object 1.

The transmitting system 5 is made up of a high frequency oscillator 11, a modulator 12, a high frequency amplifier 13, and a high frequency coil 14a on the transmitting side. A high frequency pulse outputted from the high frequency oscillator 11 is subjected to an amplitude modulation by the modulator 12 at a time of a command from the sequencer 4, and the high frequency pulse being subjected to the amplitude modulation is amplified by the high frequency amplifier 13. Then, the pulse is supplied to the high frequency coil 14a placed in proximity to the test object 1, whereby an RF pulse being an electromagnetic wave is irradiated on the test object 1.

The receiving system 6 is made up of a high frequency coil 14b on the receiving side, an amplifier 15, and a quadrature phase detector 16, and an A/D converter 17. A response electromagnetic wave (NMR signal) from the test object that is induced by an electromagnetic wave irradiated from the high frequency coil 14a on the transmitting side is detected by the high frequency coil 14b arranged in proximity to the test object 1, and the NMR signal is amplified by the amplifier 15, and then, divided into orthogonal two series of signals by the quadrature phase detector 16. Thereafter, each signal is converted into a digital amount by the A/D converter 17.

The controller 200 is provided with an imaging controller (including sequencer 4) 210 for exercising control over the gradient magnetic field generation system 3, the transmitting system 5, and the receiving system 6 following a predetermined pulse sequence, an image reconstruction unit 220 for reconstructing an image by using the NMR signal obtained by the imaging, a table controller 230 for controlling the table driving system 31, a display controller 240 for controlling a display on the display unit (display 20), a storage unit 250 for storing data necessary for processing each of the above units, and a main controller 260 for exercising overall control.

The imaging controller 210 exercises control over the gradient magnetic field generation system 3, the transmitting system 5, and the receiving system 6, via the sequencer 4, following the pulse sequence determined by the imaging method. The table controller 230 controls the movement of the table so that the table 30 is shifted in a stepwise manner by a predetermined distance between one imaging and another.

The image reconstruction unit (CPU 8) 220 inputs data from the receiving system 6, and executes processing such as signal processing and image reconstruction. Then, a resulting tomographic image of the test object 1 is displayed on the display 20, as well as recorded in the magnetic disk 18, and the like, of the external storage unit 400. The display controller 240 controls an output (display) of the image being reconstructed, and controls displaying of a GUI that is necessary for setting an imaging parameter, and for setting an imaging condition for each station, in particular, a slice condition.

The I/O unit 300 is for displaying an image of the test object and inputting various control information of the devices and information necessary for the processing carried out in the signal processing system 7. This I/O unit is made up of an operation unit such as a track ball or a mouse 23 and a keyboard 24, and a display 20 arranged in proximity to the operation unit 25. An operator controls various processing of the devices interactively via the operation unit 25, while viewing the display 20.

Figure 3:
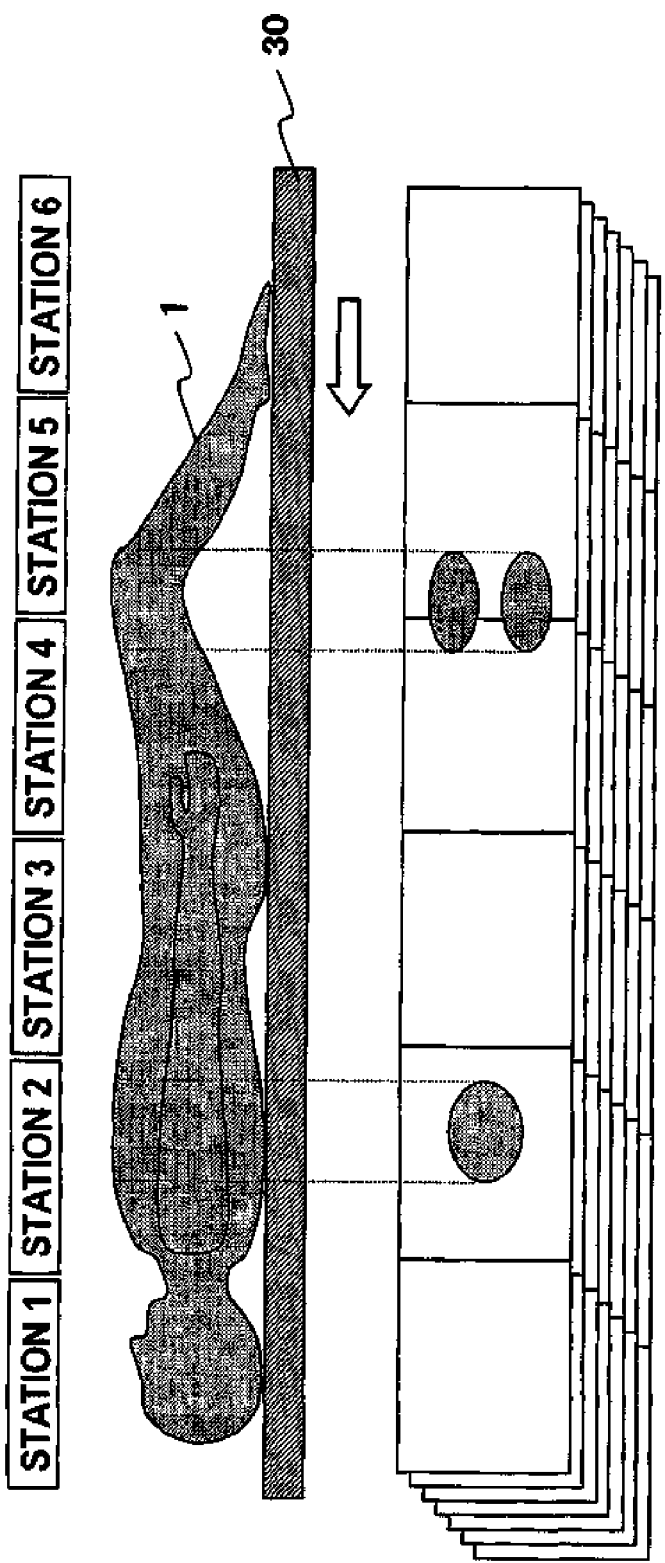
FIG. 3 illustrates imaging by the step shift method in the MRI apparatus according to the present invention.
Figure 4:
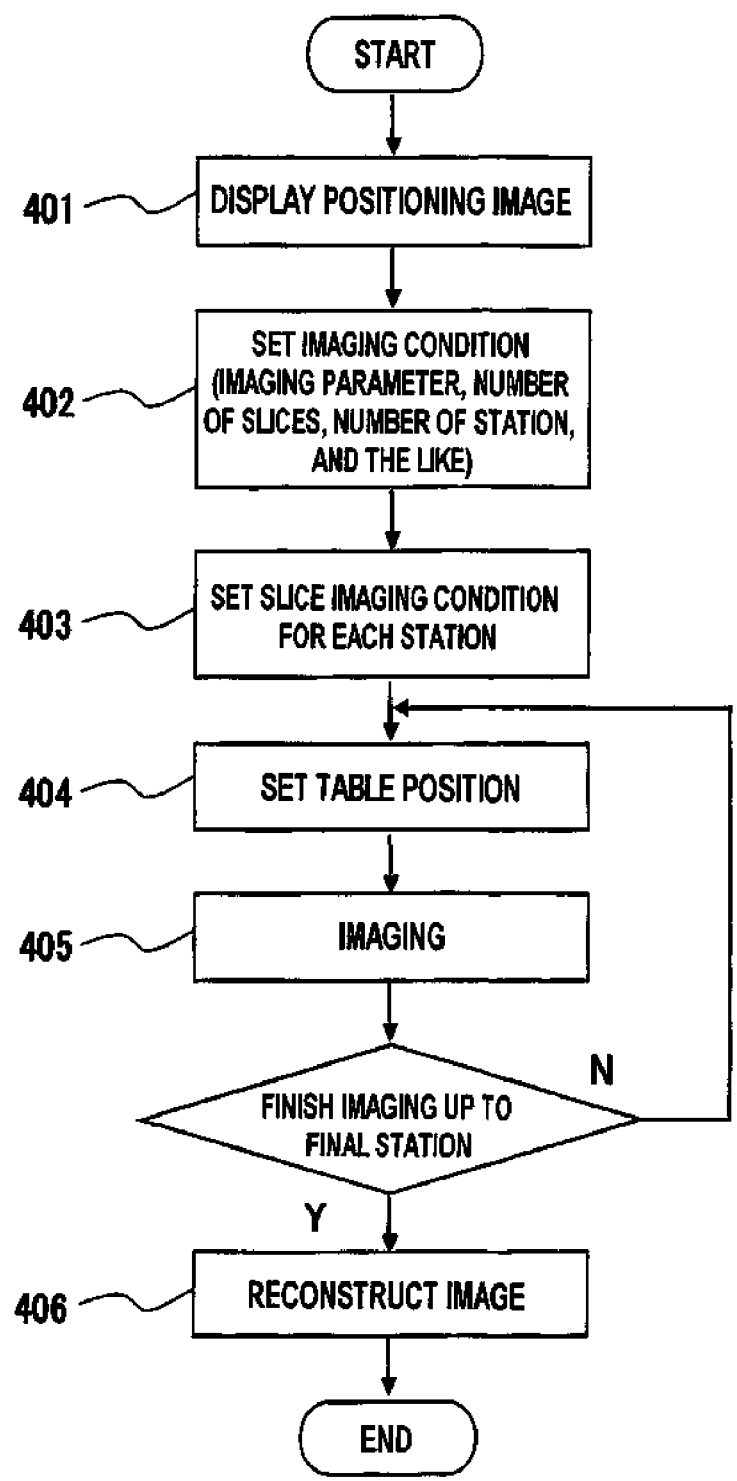
FIG. 4 is a flow diagram showing a procedure of the imaging by the step shift method according to a first embodiment of the present invention.

Next, an imaging by the step shift method will be explained, which is executed by the MRI apparatus having the configuration as described above. FIG. 3 illustrates an overview of the step shift method, and FIG. 4 shows a procedure of the step moving imaging according to the first embodiment of the present invention.

For example, as illustrated in FIG. 3, in the step shift method, a table on which the test object is laid is moved in the arrow direction, and images of a head region, a chest region, an abdominal region, a femoral region, a lower limb region, and a foot region of the test object are taken, at six table-fixed positions (the first station to the sixth station). In each station, a direction orthogonal to the table moving direction is assumed as a slice direction, and imaging of multiple slices, e.g., multislice imaging, is performed. The pulse sequence employed for the imaging is not particularly limited, and any pulse sequence can be employed, such as spin echo base sequence, gradient echo base sequence, and EPI base sequence.

In the imaging, the test object is firstly placed in the imaging space, and a sagittal image along the body axial direction is taken as a positioning image. Then, this image is displayed (step 401). Subsequently, settings are configured such as setting imaging parameters for a main scan, and setting an imaging condition including the number of stations, slice thickness, and the number of slices (step 402). Next, using the GUI displayed by the display unit, settings of the station-by-station slice imaging condition are configured (step 403). After such settings are completed, the test object is placed at the imaging position of the first station (step 404) and the imaging is started (step 405). When the imaging in the first station is finished, the table is moved (step 404), and the imaging is performed at the imaging position of the second station (step 405). Hereinafter, the imaging is performed until the sixth station. After the imaging in each of all the stations is completed, images respectively obtained in the stations are synthesized, and a multislice image having a wide field is obtained as shown in the lower part of FIG. 3 (step 406).

Figure 5:
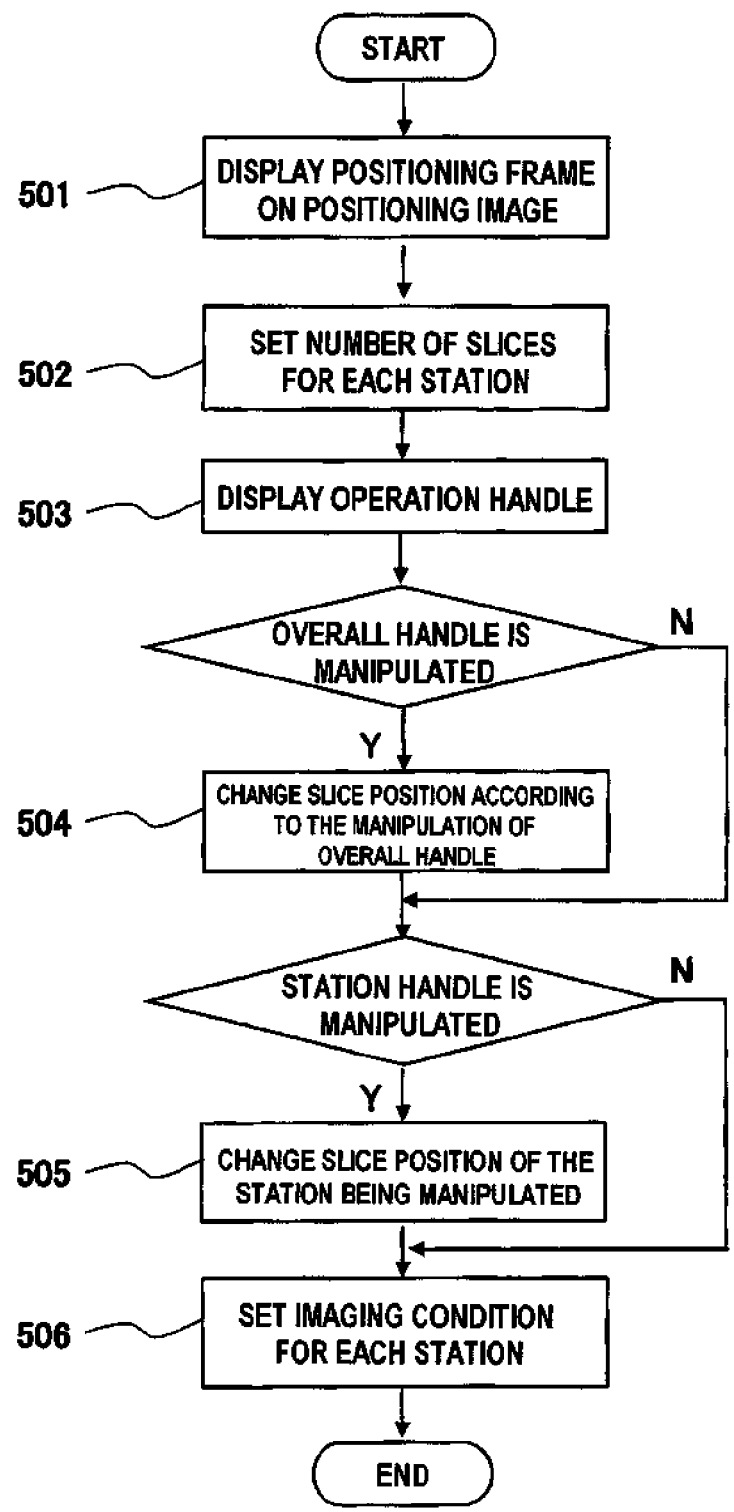
FIG. 5 is a flow diagram showing a procedure for setting a slice imaging condition.
Figure 6:
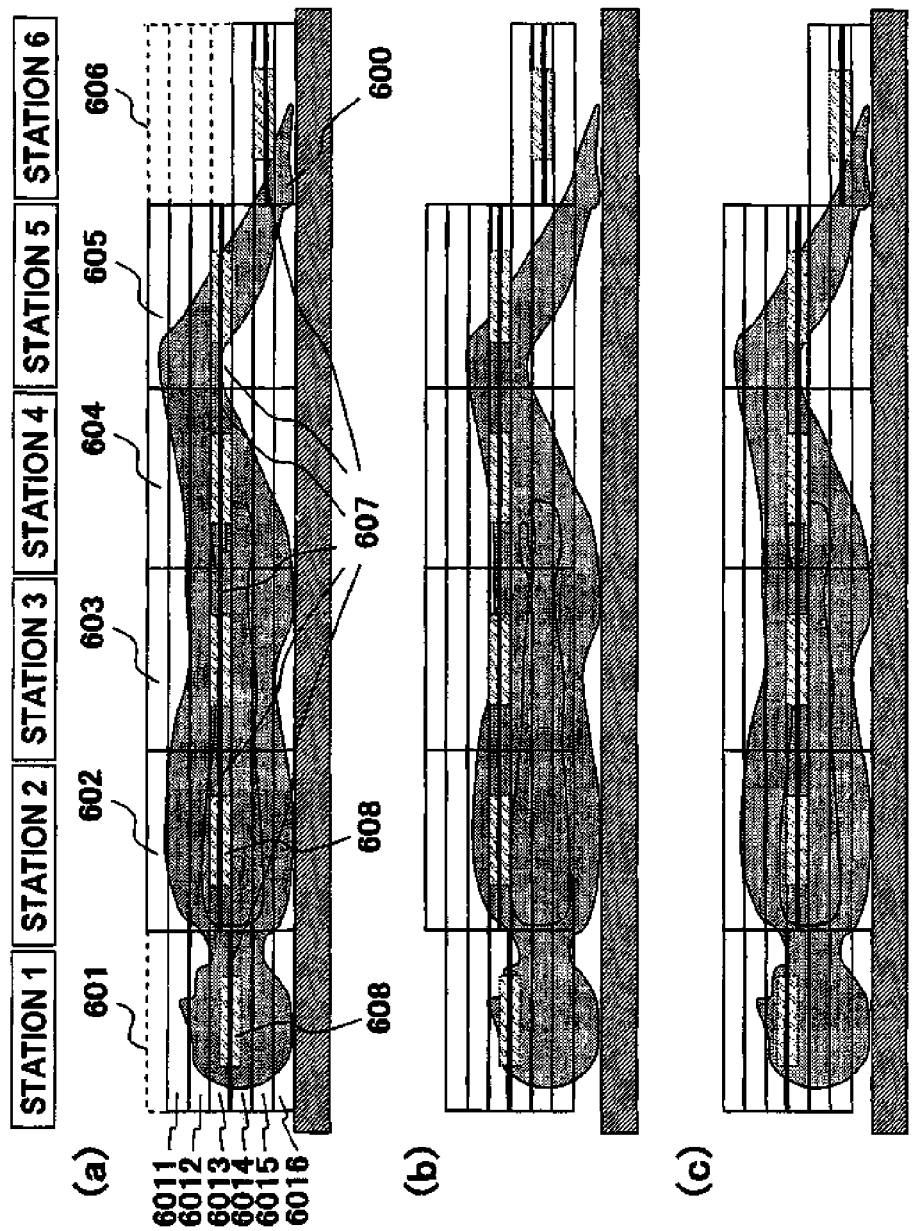
FIG. 6 illustrates GUIs for setting the slice imaging condition according to the first embodiment of the present invention.

FIG. 5 shows steps of the procedure for setting the station-by-station slice imaging condition (step 403) Setting of the slice imaging condition is carried out via the GUI displayed on the display. When the imaging condition is set in step 402, firstly according to the display controller 240, there are displayed on the display, as shown in FIG. 6(*a*), a positioning image 600, and frame lines 601 to 606 indicating slice areas determined by the slice thickness and the number of slices set in step 402 (referred to as "positioning frame") (step 501). In the embodiment as illustrated, there are displayed positioning frames corresponding to seven slices in each of the stations.

The operator manipulates the positioning frames displayed on the display, so as to delete an unnecessary slice or to add a slice. For instance, in the example shown in FIG. 6, in the station 2 to take an image of the chest region, it is necessary to take images of seven slices in order to obtain an image of the entire chest region. However, if the seven slices, being the same in number for the chest region, are set for the station 1 or the station 6, respectively for the head region and the foot region, there occurs a slice where the test object does not exist. In such a case above, a positioning frame, corresponding to the unnecessary slice in each station, may be deleted, or the like, with the manipulation of the operation unit, and thus the number of slices is determined with respect to each station (step 502). In FIG. 6(*a*), a deleted positioning frame is illustrated by a dotted line. Consequently, in the station 1 for imaging the head region, the positioning frame 601 (6011 to 6016) corresponding to six pieces of slice is displayed, and in the station 6 for imaging the foot region, the positioning frame 606 corresponding to three pieces of slice is displayed. In the remaining stations, the positioning frames 602 to 605, keeping the initial settings, are displayed. It is to be noted that the settings of the number of slices (step 502) may be configured by manipulating the positioning frame by the operator as described above, but it may be automatically configured according to a pixel value within the positioning frame. By way of example, in the image data in which the positioning image and the positioning frame are superimposed one on another, if the pixel value within the positioning frame is zero or close to zero, this positioning frame becomes a target for deletion.

The operator is further allowed to manipulate the positioning frame to change the slice thickness or the FOV, being previously configured, in addition to the aforementioned slice deletion and addition. The change of the slice thickness may be carried out by selecting one frame line of the positioning frame and moving the selected frame line in the slice direction. In addition, the change of the FOV may be carried out by moving the edge surrounding the positioning frame in the table moving direction, for instance. Those changes of the slice thickness and the FOV may be executed by a manipulation being independent in each station. Alternatively, manipulation of one positioning frame may allow a change in all of the stations in a linked manner. By way of example, in the case of changing the FOV, when the positioning frame of one station is widened or narrowed, the adjacent position frame may be narrowed or widened along therewith.

As thus described, when the number of slices (the slice thickness and the FOV are changed, if necessary) of each station is determined, a GUI for changing the slice position within the station is displayed. The illustrated example displays an overall handle 607 for integrally moving the positioning frame 601 to 606 of the total imaging area, and a station handle 608 for integrally moving all the positioning frames within one station, with respect to each station (step 503). These handles 607 and 608 can be moved up and down by operations such as clicking and dragging by the mouse, and the positioning frames are moved along with the movement of the handles (steps 504 and 505). By way of example, when the overall handle 607 is moved up, the positioning frames 601 to 606 are moved upwardly along therewith, and FIG. 6(*b*) shows a resultant display. The operation of the station handle 608 is limited so that the vertical moving distance is discrete and the positioning frame can be moved in such a manner that the positioning frame after the movement is aligned with another positioning frame of the adjacent station. For example, the operation of the station handle 608 of the station 1 can be performed in a unit of space of the positioning frame that corresponds to the slice thickness. When the station handle 608 is moved upwardly, the positioning frames 6011 to 6016 within the station 1 are moved upwardly along therewith, and FIG. 6(*c*) shows the resultant display.

The overall handle 607 and the station handle 608 are manipulated as described above, and the positioning frame is set, station by station, on the positioning image 600 of the test object that is displayed in a manner superimposed. Thereafter, the information of the positioning frames (the number and position thereof), which is set via the I/O unit 300, is passed to the imaging controller 210. Then, the number of imaging slices and the imaging slice position respectively corresponding to the number and the position of the positioning frames are set as the slice imaging condition (step 506), and imaging in each station is started under this slice imaging condition. As for the image data of the slice obtained by the imaging in each station, the slice images located on the same position in the slice direction (in the figure, vertical direction) are synthesized, and an image of the total body of the test object at this position is obtained. The images at all the positions are synthesized in the same manner, and a multi-slice image of the test object is obtained.

FIG. 6 shows a case where there is no overlapping of FOV in the slice width direction between the stations, i.e., the table moving distance T is equal to the image width W in the table moving direction. However, in the range satisfying the condition of W≧T, the FOV size in the slice width direction can be changed. In the case where W>T, it is possible to obtain overlapping data in the range of [W-T] between the adjacent stations. This overlapping data can be used as correction data for enhancing image continuity between the stations, when the images are synthesized.

According to the present embodiment as thus described, it is possible to set an optimum slice imaging condition, i.e., an optimum number of slices and slice position with respect to each station, by using the positioning frames displayed in a superimposing manner on the positioning image of the test object, and the slice-setting-use GUI. Therefore, it is possible to eliminate imaging of the slice where the test object does not exist, and thereby accomplishing an efficient wide field imaging. In addition, the moving distance of the positioning frame is limited to the frame basis, therefore, in synthesizing images, the slice images of each of the stations are continuously combined as they are, and thereby obtaining one piece of wide field image.

In the aforementioned embodiment, there is explained a case where the slice position is determined under the condition that the moving direction and moving distance of the positioning frame are restricted. If a processing such as interpolating in the image reconstruction is combined therewith, it is possible to move the positioning frame more freely.

Figure 7:
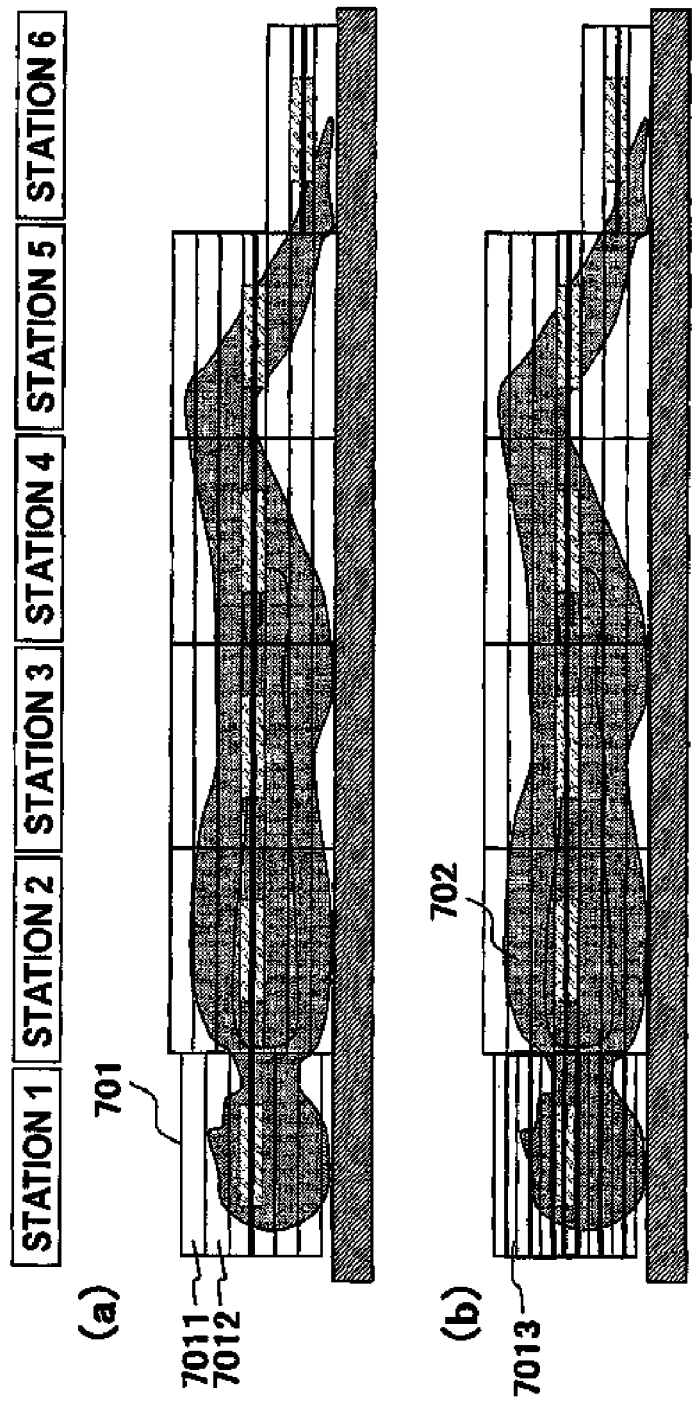
FIG. 7 illustrates GUIs for setting the slice imaging condition according to a second embodiment of the present invention.

Hereinafter, another embodiment will be explained, where the manipulation of the positioning frame is designed in a different manner. FIG. 7 illustrates a display example according to the second embodiment. The present embodiment is the same as the first embodiment in the point that imaging of the positioning image, setting of the imaging condition, and setting of the station-by-station slice imaging condition are performed according to the flow shown in FIG. 4. It is also the same that in setting the station-by-station slice imaging condition (step 403) the positioning image, the positioning frame for setting the slice, the overall handle, and the station handle are displayed.

However, in the present embodiment, the movement of the positioning frame by the station handle can be carried out in a continuous fashion, and the positioning frame within the station can be moved to any position in the vertical direction. In the example shown in FIG. 7(*a*), the positioning frame 701 of the station 1 is set at a position being displaced in the vertical direction, with respect to the positioning frame of the adjacent station 2. The positioning frame information set via the I/O unit 300 as described above is passed to the imaging controller 210, and here, the imaging slice position and the number of slices are set station by station.

Figure 8:
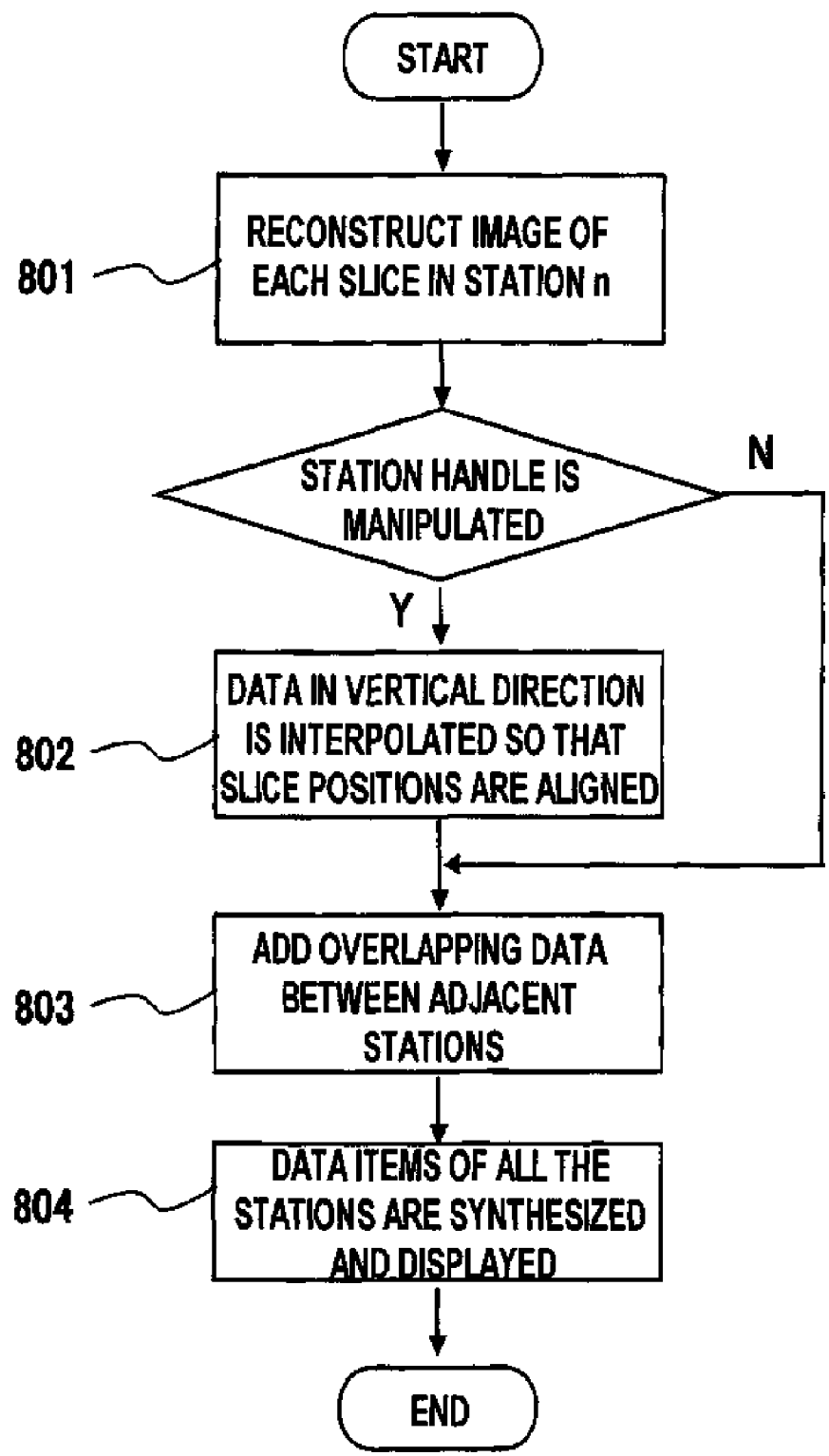
FIG. 8 is a flow diagram showing a procedure for an image reconstruction according to the second embodiment of the present invention.

In performing the imaging (step 405), the imaging is performed under the slice imaging condition being configured as described above. However, the slice image of the station 1 obtained by the imaging is displaced in the slice direction from the slice image of another station, and one piece of wide field slice image cannot be obtained only by linking the images as they are. Therefore, in the present embodiment, the image reconstruction unit 220 uses data of each slice in the station 1 and creates image data at the slice position aligned with the slice position of another station. Specifically, as shown in the flow of FIG. 8, an image of each slice is reconstructed with respect to each station (step 801). In the station where there is a movement in the slice direction, by using the data of slice 7011 and the data of slice 7012, for example, the data of the slice 7013, which is located therebetween and at the position aligned with the slice of another station is obtained by interpolation (step 802). A publicly known technique is employed for the interpolation, for example, spline interpolation. After image data items at the same slice position are created as to all the stations, those image data items are linked to generate one piece of wide field image as to the slice position. If there is overlapping data between the adjacent stations, weighted averaging or the like may be carried out, and the data items are synthesized (steps 803 and 804).

According to the present embodiment, a slice setting more suitable for each part of the test object becomes available.

Next, a third embodiment of the present invention will be explained. In the present embodiment, in setting the station-by-station slice imaging condition (step 403), the slice settings are configured including the setting of the slice surface angle, so as to fit a shape of the test object, with respect to each station.

Figure 9:
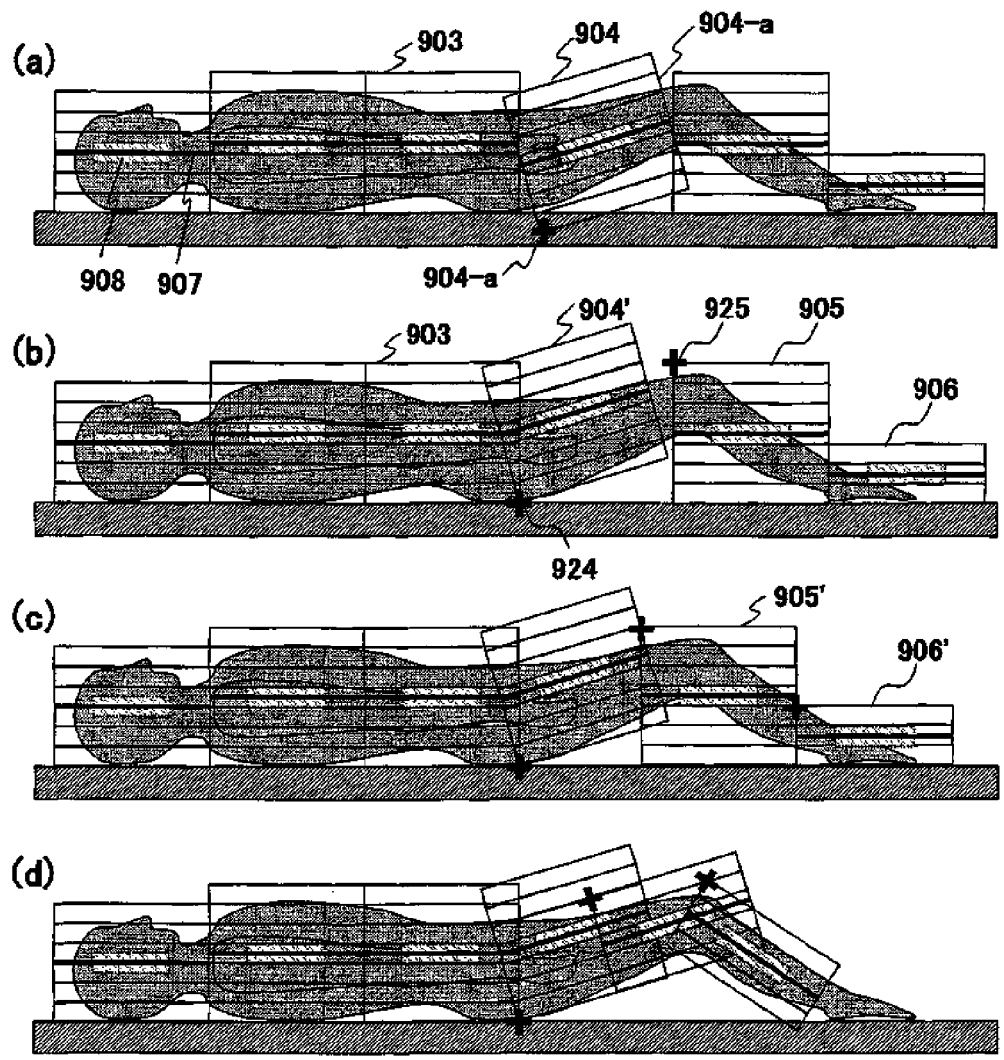
FIG. 9 illustrates GUIs for setting the slice imaging condition according to a third embodiment of the present invention.

FIG. 9 illustrates a display example according to the third embodiment. Also in the present embodiment, the slice position setting is performed by using the positioning frame displayed in a superimposed manner on the positioning image of the test object, the overall handle 907, and the station handle 908. However, the positioning frame is designed to be rotatable and movable in parallel independently in each station. In the example as shown in FIG. 9, any one of the four edges surrounding the positioning frame 904, for example, a side edge, is assigned as the rotation handle 904-*a* for the rotational operation. According to the input means such as a mouse, the rotation handle 904-*a* of the station 4 is manipulated, so as to fit the shape of the test object (the inclination of the femoral region) (FIG. 9(*a*)). With the rotation of the positioning frame 904, a portion without any overlapping appears between the positioning frame 904 and the positioning frame 903 of the station 3. Therefore, the end-point 924 is shifted by manipulating the station handle 908 of the positioning frame 904, so that all the positioning frames overlap one on another between the positioning frame 904 and the positioning frame 903. Since there is a distance from the positioning frame 905 of the station 5, (b), the positioning frame 905 of the station 5 is adjusted. This adjustment is made so that the end-point 925 of the positioning frame 905 is connected to any end-point belonging to the positioning frame 904', for instance. As a result of this operation, the positioning frame 905 moves automatically in the horizontal direction, and it is linked with the positioning frame 904' of the station 4, (c). In moving the positioning frame 905 of the station 5, it is further possible that the positioning frame 905 of the station 5 and the positioning frame 906 of the station 6 are grouped, and the positioning frame 906 of the station 6 is moved along with the movement of the positioning frame 905 of the station 5.

Furthermore, if necessary, the positioning frames of other stations (station 5 and/or station 6) are rotated, so as to fit the curved state of the test object. In this case, operations such as the rotation, parallel shift of the positioning frame of the station, and deletion of the slice may be combined and performed. For instance, as shown in FIG. 9(*d*), the slice positions of the stations 4 to 6 are adjusted so that imaging of the femoral region and the lower limb region can be performed at a slice position and at an angle fitting the curved state of those regions.

After the position and the angle of the positioning frame in each station are set as described above, this information is passed to the imaging controller 210. The imaging controller 210 sets a gradient magnetic field condition for each station, according to the position and the angle of the positioning frames, and controls the imaging unit 100 so that the imaging is performed at a slice position and in the slice direction corresponding to the positioning frame. Here, since the distance between the stations is varied by the rotation or the parallel shift of the slice position, it is also necessary to change the table moving distance between the stations. The imaging controller 210 and the table controller 230 calculate a table moving distance between the stations, based on the information of this slice position (a coordinate value of a central slice (the midpoint thereof) of each station) in the table moving direction. Then, a distance by which the table 30 is to be moved after the end of imaging of one station is controlled. In imaging of each station, the imaging is performed using the number of slices, slice position, and slice direction, which are set with respect to each station.

After the imaging, the images obtained in each of the stations are synthesized to generate a wide field image. In combining the images, as for the station in which the slice direction is set to fit the curved part of the test object, the images are also joined together at the slice position where the positioning frame is continuous. In this case, if there is unnecessary data, such data is deleted. If there is overlapping data, it is utilized as correction data for improving the image quality at the joint of images. In addition, if the slice thickness of a station is different from the slice thickness of the adjacent station in the slice direction, data at the associated position is obtained by interpolation, just like the case where the slice position is displaced one from another (the second embodiment), and the images are synthesized by using the data being interpolated.

Figure 10:
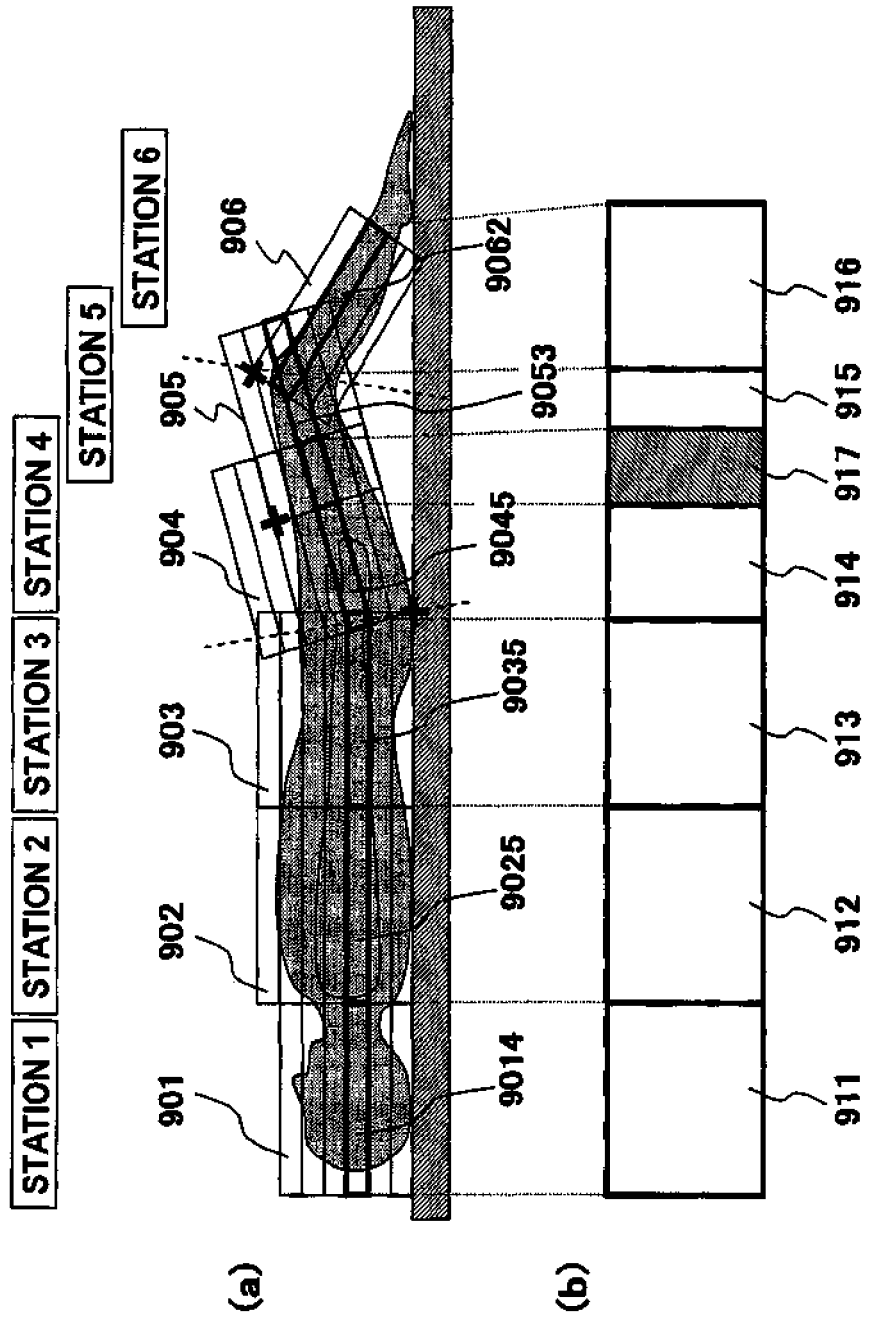
FIG. 10 illustrates the image reconstruction according to the third embodiment of the present invention.

FIG. 10 shows an example of image synthesis according to the present embodiment. This example shows the case where the imaging is performed setting the slice imaging condition as illustrated in FIG. 9(*d*) In each of the station 1 to 6, there are obtained slice image data in number corresponding to six positioning frames 901, seven positioning frames 902, seven positioning frames 903, seven positioning frames 904, five positioning frames 905, and four positioning frames 906. The slices in the stations 4 to 6 are inclined with respect to the horizontal direction, and the slices of the station 5 intersect the slices of the station 6.

The image reconstruction unit 220 combines the slices having continuous positioning frame lines, among the multiple slices in each of the stations, thereby creating one piece of total body image. In the example being illustrated, the slice image 911 corresponding to the positioning frame 9014, the slice image 912 corresponding to the positioning frame 9025, the slice image 913 corresponding to the positioning frame 9035, the slice image 914 corresponding to the positioning frame 9045, the slice image 915 corresponding to the positioning frame 9053, and the slice image 916 corresponding to the positioning frame 9062 are joined together. There exists unnecessary data on the joint between the intersecting slices, i.e., respectively on the joint between the image 913 and the image 914, and the joint between the image 915 and the image 916. Therefore, the image reconstruction unit 220 takes appropriate procedures, such as removing this kind of unnecessary data. At a joint part of continuous slices, where the data items are overlapping, for example, the joint 917 between the image 914 and the image 915, one of the overlapping data items is removed, or an average is obtained to improve the image quality of the joint.

According to the present embodiment, the slice position and the slice direction can be set, taking a posture of the test object into account. Therefore, the total body imaging can be performed much efficiently. Even in the case where the posture is curved, it is possible to obtain a tomographic image along the body axis of the test object.

In each of the embodiments described above, there has been explained a case where a basic slice surface is parallel to the moving direction of the test object, i.e., the slice direction is orthogonal to the moving direction of the test object. However, it is further possible to apply the present invention to the case where a slice surface is selected in such a manner as intersecting the moving direction of the test object.

Figure 11:
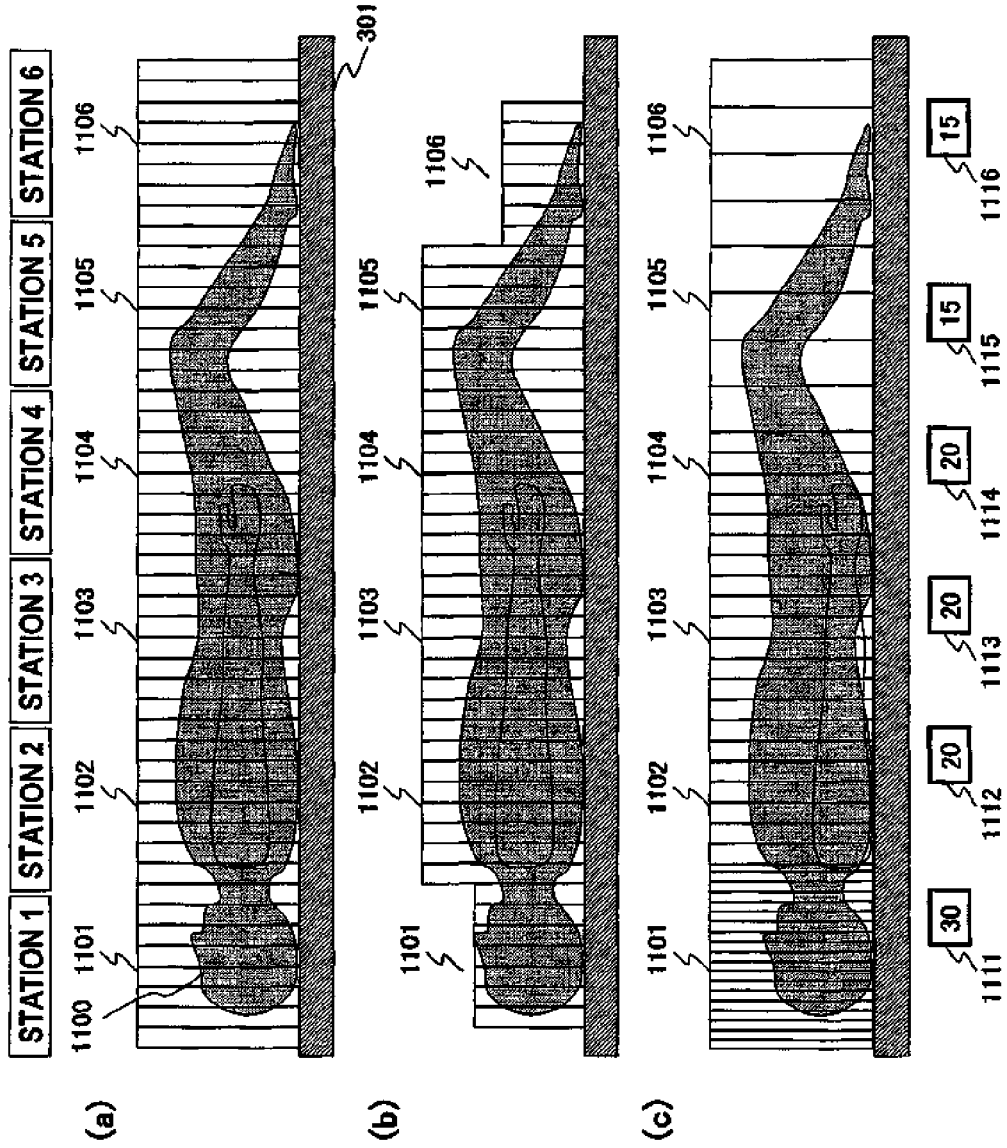
FIG. 11 illustrates GUIs for setting the slice imaging condition according to a fourth embodiment of the present invention.

Hereinafter, as a fourth embodiment, another case will be explained, in which imaging is performed assuming the direction orthogonal to the moving direction of the test object as a slice surface in each station. Also in the present embodiment, a procedure for setting the station-by-station slice condition is the same as the embodiment as shown in FIG. 4. However, in the present embodiment, in step 402 for setting the imaging condition, the imaging sequence is configured in such a manner that the slice direction is set to be the bed moving direction. In step 402, after the settings of such imaging parameters and the settings of basic imaging conditions such as the number of slices and the number of stations are configured, there are shown on the display as illustrated in FIG. 11(*a*), a positioning image 1100, and the positioning frames 1101 to 1106 indicating the slice areas determined by the slice thickness and the number of slices configured in step 402. In this initial setting stage, the slice imaging conditions (number of slices, slice thickness, FOV on the slice surface) are equivalent in each station. In FIG. 11, each section within the positioning frame corresponds to a slice, but the figure is simplified and the number of sections is less than an actual number of slices. Though not illustrated here, it is also possible to display an overall handle for changing the whole positioning frames 1101 to 1106 and a station handle for changing the respective positioning frames independently, and the like. It is further possible to assign a function as a handle to the four edges surrounding the positioning frame.

Here, it is to be noted that in the initial station 1 and in the last station 6, there may be a slice surface where the test object does not exist, depending on the height of the test object. In addition, as for the FOV, in the stations 2 and 3 for imaging the abdominal region and the chest region, a ratio of the test object is large in the field of view, but in the station 1 and 6 for imaging the head region and the foot region, a ratio of the test object is small in the field of view. Given those factors above, as shown in FIG. 11(*b*), a predetermined positioning frame is reduced by manipulating the operation unit to change the number of slices and the FOV in each station (step 403). Specifically, the vertical and horizontal size of the positioning frames 1101 to 1106 are changed to be suitable for the test object image being displayed, according to a manipulation such as clicking or dragging of the mouse. With those operations, the number of slices and the FOV are set to fit the position and the size of the test object, with respect to each station.

Accordingly, the information of the positioning frame (number of slices and FOV), being set via the I/O unit 300 is passed to the imaging controller 210, and this information is set as the slice imaging condition. Then, under this slice imaging condition, imaging in each station is started (steps 404 and 405). In the station where the FOV is reduced, the imaging is performed while the sequence repetition time (phase encoding number) is reduced. Accordingly, it is possible to shorten the imaging time. Instead of shortening the imaging time, the addition number may be increased or the repetition time TR may be extended. Accordingly, S/N ratio of the image can be enhanced. Alternatively, if the phase encoding number is not changed and the phase encoding step is turned down, it is possible to obtain an image having a high spatial resolution.

Finally, image data items of the slices are synthesized, which are obtained by imaging in each station, so as to acquire a total body image of the test object (step 406). If the image spatial resolution is different by station, interpolation or the like is carried out for the image data in the station having a large FOV of the test object, and the spatial resolution is equalized for each station. Thereafter, the image data items are synthesized.

FIG. 11(b) illustrates a case where the number of slices and the FOV of each station are changed. In addition to changing these elements, it is also possible to change the slice thickness. In this case, before or after displaying the GUI (positioning frame) for changing the number of slices and the FOV as described above, a GUI for setting the slice thickness is displayed. By way of example, when the positioning frames 1101 to 1106 are displayed as shown in FIG. 11(c) setting boxes 1111 to 1116 are displayed for setting the number of slices or the slice thickness with respect to each station. In this instance, the number of slices or the slice thickness configured in the initial settings is displayed in each setting box, and it is designed so that the numerical value can be changed. The slice thickness is changed by increasing or decreasing this numerical value with respect to each station. Instead of inputting the number of slices or the slice thickness, a ratio to the basic slice thickness (the slice thickness set in step 402) may be inputted, for example, a numeric value such as 150% and 80%. Sections reflecting the inputted slice thickness are displayed in the positioning frames 1101 to 1106. It is to be noted here that the sections are just schematically illustrated, and the number of sections are not the same as the actual number of slices.

After the slice thickness is set for each station as thus described, as shown in FIG. 11(b), the positioning frames 1101 to 1106 may be reduced for the purpose that the imaging range becomes optimum with respect to each station. Accordingly, by way of example, in the station where a portion as to which a blood stream should be observed in particular is located, imaging is performed with the slice thickness made thinner, and it is possible to obtain an image having a favorable resolution in the slice direction. As for the portion having less diagnostic importance compared to the other portions, the slice thickness is made thicker and imaging time can be shortened.

Next, a fifth embodiment of the present invention will be explained. Also in the present embodiment, in the imaging sequence being initially set, a direction orthogonal to the moving direction of the test object is assumed as the slice surface, and this is the same as the fourth embodiment. The procedure for setting the slice condition for each station is the same as the embodiment as shown in FIG. 4. The present embodiment features that in step 403, there is achieved a lot of flexibility in setting the slice, according to the operations such as a slice rotation and a slice parallel shifting by using a GUI.

Figure 12:
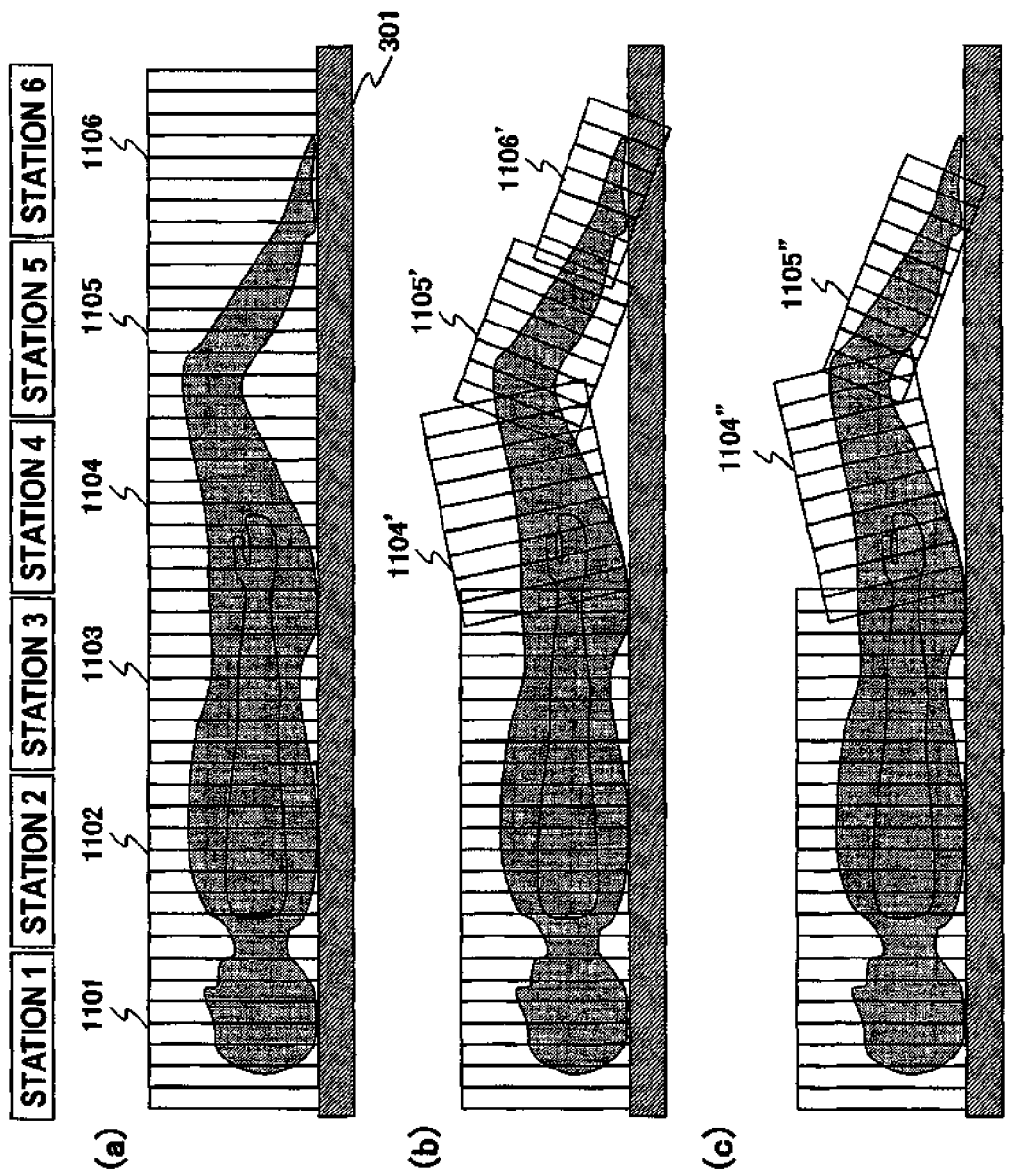
FIG. 12 illustrates GUIs for setting the slice imaging condition according to a fifth embodiment of the present invention.

FIG. 12 shows an example of the GUI. Also in the present embodiment, when the imaging condition is set according to step 402 as shown in FIG. 4, the positioning image 1100 and the positioning frames 1101 to 1106 indicating the slice areas that are determined by the slice thickness and the number of slices set in the step 402 are displayed on the display unit as shown in FIG. 12(a).

Next, the positioning frame is rotated following the posture of the test object with respect to each station. In the example as shown in FIG. 12(b), the positioning frames 1104 to 1106 of the stations 4 to 6 are manipulated by the input means such as a mouse, and the positioning frames are rotated in such a manner that they fit the bent foot region of the test object. In the example being illustrated, even when the positioning frames are rotated, no data missing parts appear from the positioning frames 1104' to 1106' after the rotation. However, if a part having no overlapping occurs due to the rotation, the positioning frame is subjected to parallel shift in the horizontal direction or in the vertical direction, so as to avoid the data missing. Subsequently, the vertical and horizontal size of the positioning frame is enlarged or reduced as appropriate, and the number of slices and the FOV within the frame are adjusted.

By way of example, as shown in FIG. 12(c), it is possible to extend the lateral size of the positioning frames 1104" and 1105" of the station 4 and the station 5, so that the slice position fits the bent state of the femoral region and the lower limb region. Further in this case, similar to the embodiment as shown in FIG. 11(c), a function to change the slice thickness with respect to each station may be added.

Also in this embodiment, similar to the third embodiment, along with the rotation or the horizontal shift of the slice position, a distance between the stations is changed. Therefore, it is necessary to change the moving distance of the table between the stations. The imaging controller 210 and the table controller 230 calculate a travel distance between the stations so that a center position of the positioning frame newly set becomes a static magnetic field center. Then, in step 404 for setting the table position and in step 405 for imaging in FIG. 4, the table is moved by a station distance having been changed, and the imaging is performed at each station. After the imaging, the images being obtained from each of the stations are synthesized to create a wide field image. On this occasion, if there is unnecessary data, it is deleted. If there is overlapping of data, it is used as correction data for improving the image quality at the joint of the images.

According to the present embodiment, in addition to the change of the number of slices and the FOV by the operation for changing the size of the positioning frame, the slice direction and the station position are made changeable by the operation for changing the slice angle and position. Therefore, it is possible to make the imaging more efficient, fitting the shape and posture of the test object.

Each embodiment of the present invention has been explained, taking the multi-slice imaging as an example. However, the present invention can be applied to 3D imaging using a slice encoding. In this case, the entire positioning frame of each station corresponds to a slab excited at one-time, and the number of the positioning frames is equivalent to the slice encoding number. The 3D imaging is useful for imaging a total-body Magnetic Resonance Angiography (MRA), and the like. On this occasion, the imaging time can be shortened by reducing the slice encoding number at a portion such as the foot region where peripheral blood vessels are thin.

In addition, when the interpolation is carried out in the 3D imaging, as shown in FIG. 13, by way of example, the matrix size of k-spatial data (a) is enlarged in the slice encoding direction, to obtain k-spatial data (b) with zero padding. When an image is reconstructed from this data b), image data (c) is obtained that has image data (c) with the same slab thickness as image data (d) that is reconstructed from the original k-spatial data (a), but the number of slices is increased. The slice thickness is thin in this image data (c). Interpolation is carried out based on the slices of this image data (c), by using the spline interpolation in the image space.

According to the present invention, in the imaging by the step shift method, the slice imaging condition can be set easily and optionally, with respect to each station, and a total-body imaging can be performed within a shorter imaging time, in such a manner as fitting the imaging to the size and the posture of the test object.

What is claimed is:

1. A magnetic resonance imaging method for moving a test object in a stepwise manner among multiple stations and taking images of different areas of the test object on the respective stations, so as to acquire an image of a wide range of the test object, comprising,
    a slice imaging setting step for performing a slice imaging setting by arranging a positioning frame of a slice for each of the stations, using a positioning image that is previously acquired and includes the wide range,
    an imaging step for performing imaging in each of the stations based on the slice imaging setting of each of the stations, and
    a synthesizing step for synthesizing a test object image of the wide range by using a nuclear magnetic signal obtained by the imaging step, wherein,
    in the slice imaging setting step, the positioning frame being arranged is adjusted according to how to place the test object.

2. The magnetic resonance imaging method according to claim 1, wherein,
    in the slice imaging setting step, the positioning frame is shifted in the slice direction.

3. The magnetic resonance imaging method according to claim 2, wherein,
    shifting of the positioning frame in the slice direction is performed in such a manner that positions of the slices between the stations being adjacent are approximately aligned with each other in the slice direction.

4. The magnetic resonance imaging method according to claim 2, wherein,
    shifting of the positioning frame in the slice direction is performed discretely using a slice thickness as a unit.

5. The magnetic resonance imaging method according to claim 1, wherein,
    in the slice imaging setting step, the positioning frame is shifted in parallel with a body axis direction of the test object.

6. The magnetic resonance imaging method according to claim 1, wherein,
    in the slice imaging setting step, the positioning frame is shifted rotationally.

7. The magnetic resonance imaging method according to claim 1, wherein,
    in the slice imaging setting step, a field-of-view of the positioning frame is changed according to an area of the test object within the station.

8. The magnetic resonance imaging method according to claim 1, wherein,
    in the slice imaging setting step, a slice thickness of the positioning frame is changed.

9. The magnetic resonance imaging method according to claim 1, wherein,
    in the slice imaging setting step, with shifting or transformation of one positioning frame, an adjacent positioning frame is also shifted or transformed.

10. The magnetic resonance imaging method according to claim 1, wherein,
    in the slice imaging setting step, shifting or transformation of each of the positioning frames is independently performed.

11. The magnetic resonance imaging method according to claim 1, wherein,
    in the slice imaging setting step, a slice direction is set in a vertical direction with respect to a moving direction of the test object.

12. The magnetic resonance imaging method according to claim 1, wherein,
    in the slice imaging setting step, a slice direction is set in a parallel direction with respect to a moving direction of the test object.

13. The magnetic resonance imaging method according to claim 1, wherein,
    in the slice imaging setting step, a frame line of the positioning frame is added or deleted according to an area of the test object, and in response thereto, a number of slices or a slice-encoding number is each increased or decreased.

14. The magnetic resonance imaging method according to claim 1, wherein,
    in the imaging step, a distance between the stations is controlled based on a configuration of the positioning frame being set in the slice imaging setting step.

15. The magnetic resonance imaging method according to claim 1, wherein,
    in the image synthesizing step, based on image data of multiple slices obtained in one station, images are created at slice positions respectively associated with multiple slice positions of another station adjacent to the one station.

16. The magnetic resonance imaging method according to claim 1, wherein,
    in the image synthesizing step, in a three-dimensional imaging, by using each slice image of which a number of slices is increased after a reconstruction with a slice encoding number being increased, an image being associated with a slice position of an adjacent station is created.

17. A magnetic resonance imaging apparatus comprising,
    a static magnetic field generation means for generating a static magnetic field,
    a transfer means for moving a test object in a static magnetic field space generated by the static magnetic field generation means,
    an imaging means for moving the test object in a stepwise manner among multiple stations and taking an image using a nuclear magnetic resonance,
    an image reconstruction means for creating an image of a wide range of the test object based on the nuclear magnetic resonance signal acquired in each of the multiple stations, a control means for controlling the transfer means, the imaging means, and the image reconstruction means, a slice imaging setting means for performing a slice image setting by arranging a slice positioning frame for each of the stations, using a positioning image previously acquired and including the wide range, and, an input means for inputting a directive to the slice imaging setting means, and, the control means further exercising control so that the imaging means takes an image of the slice that is set by the slice imaging setting means, wherein, the slice imaging setting means adjusts the positioning frame being arranged, based on the directive inputted from the input means.

18. The magnetic resonance imaging apparatus according to claim 17, wherein, the slice imaging setting means comprises a first handle for simultaneously shift the positioning frames of at least two stations.

19. The magnetic resonance imaging apparatus according to claim 17, wherein, the slice imaging setting means comprises a second handle for shifting the positioning frame each independently for each of the stations.

20. The magnetic resonance imaging apparatus according to claim 17, wherein, the positioning frame is configured in such a manner as rotationally movable.

21. The magnetic resonance imaging apparatus according to claim 17, wherein, the positioning frame is configured in such a manner that a field-of-view of the positioning frame is changeable.

22. The magnetic resonance imaging apparatus according to claim 17, wherein, the control means controls a step moved distance of the transfer means according to the slice imaging setting for each of the stations.

* * * * *